(12) United States Patent
Epstein

(10) Patent No.: US 6,394,975 B1
(45) Date of Patent: May 28, 2002

(54) METHOD TO APPLY COMPOSITIONS TO A SURFACE

(75) Inventor: Gordon H. Epstein, Fremont, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/863,883

(22) Filed: May 28, 1997

Related U.S. Application Data

(62) Division of application No. 08/703,148, filed on Aug. 29, 1996, now Pat. No. 5,879,340, which is a continuation of application No. 08/645,464, filed on May 13, 1996, which is a continuation of application No. 08/370,793, filed on Jan. 10, 1995, now Pat. No. 5,648,265, which is a division of application No. 08/090,587, filed on Jul. 12, 1993, now Pat. No. 5,405,607, which is a division of application No. 07/372,443, filed on Jun. 23, 1989, now Pat. No. 5,226,877.

(51) Int. Cl.[7] .................................................. A61M 3/00

(52) U.S. Cl. ........................... 604/43; 604/82; 604/289; 604/290; 604/311; 604/313; 604/902; 222/145.2

(58) Field of Search ................................ 606/213, 214; 604/35–38, 28, 43, 82, 83–84, 181, 187, 191, 289, 290, 310, 311, 313, 315, 540, 542–543, 902; 122/129, 130, 135, 136, 137, 145.1, 145.2, 145.5

(56) References Cited

U.S. PATENT DOCUMENTS

| 1,889,425 A | | 11/1932 | Sorensen | |
| 2,112,160 A | * | 3/1938 | Johnson | |
| 2,576,766 A | | 11/1951 | Sokolik | |
| 2,812,765 A | | 11/1957 | Tofflemire | |
| 3,065,749 A | | 11/1962 | Brass | 604/35 |
| 3,144,868 A | | 8/1964 | Jascalevich | 604/43 |
| 3,208,145 A | | 9/1965 | Turner | |
| 3,626,928 A | | 12/1971 | Barringer | |
| 3,771,522 A | | 11/1973 | Waysilk | 604/39 |
| 3,949,748 A | | 4/1976 | Malmin | |

(List continued on next page.)

FOREIGN PATENT DOCUMENTS

| DE | 2605005 | * | 9/1976 | ................. 604/902 |
| WO | 8704913 | * | 8/1987 | ................. 604/902 |

OTHER PUBLICATIONS

McCarthy et al., Barium–Impregnated Fibrin Glue: Application to a Bleeding Duodenal Sinus, Mayo Clinic Pros., vol. 62, pp. 317–319, 1987.*

Casillas et al., British J. Haematology (1982) 50:665–672.

Epstein, G.H. et al., *Anals. Otol. Rhinol and Laryngol*, (1986), vol. 95, pp. 40–45.

Feldman, M.C., et al., *Arch. Otolaryngol—Head and Neck Surg.*, (1988), vol. 114, pp. 182–185.

Feldman, M.C. et al., *Arch. Ophthalmol.*, (1987), vol. 105, pp. 963–967.

Feldman, M.C. et al., *M.J. Otolog.*, (1988), vol. 9, pp. 302–305.

Harker, L.A., et al., *New England J. Med.*, (1972), vol. 287, pp. 999–1005.

Kazal, L.A. et al., *Proc. Sec. Exp. Biol. Med.*, (1963) pp. 989–994.

(List continued on next page.)

*Primary Examiner*—Richard K. Seidel
*Assistant Examiner*—Jeremy Thissell
(74) *Attorney, Agent, or Firm*—Oppenheimer, Wolff & Donnelly

(57) ABSTRACT

A process and apparatus for one-step preparation of fibrinogen adhesive by polyethylene glycol-mediated precipitation from plasma are disclosed. The methods and apparatus of the invention permit preparation of autologous fibrinogen adhesive composition from the patient during surgery, and can be applied generally to provide such compositions. Also disclosed are an apparatus and method for application of sealant comprising this fibrinogen adhesive composition.

21 Claims, 4 Drawing Sheets

U.S. PATENT DOCUMENTS

| | | | |
|---|---|---|---|
| 4,040,420 A | 8/1977 | Speer | 604/82 |
| 4,043,042 A | 8/1977 | Perfect | |
| 4,223,676 A | 9/1980 | Wuchinich et al. | |
| 4,266,545 A | 5/1981 | Moss | 604/146 |
| 4,270,525 A | 6/1981 | Furihata | |
| 4,298,598 A | 11/1981 | Schwarz et al. | |
| 4,299,221 A | 11/1981 | Phillips et al. | |
| 4,359,049 A | 11/1982 | Redl | |
| 4,362,567 A | 12/1982 | Schwarz et al. | |
| 4,377,572 A | 3/1983 | Schwarz et al. | |
| 4,397,640 A | 8/1983 | Haug et al. | |
| 4,414,976 A | 11/1983 | Schwarz et al. | |
| 4,427,650 A | 1/1984 | Stroetmann | |
| 4,445,517 A | 5/1984 | Feild | |
| 4,519,385 A | 5/1985 | Atkinson et al. | |
| 4,573,979 A | 3/1986 | Blake | |
| 4,617,013 A | 10/1986 | Betz | |
| 4,631,055 A | 12/1986 | Redl et al. | 604/82 |
| 4,670,009 A | 6/1987 | Bullock | 604/902 |
| 4,696,669 A | 9/1987 | Menhusen | |
| 4,708,717 A * | 11/1987 | Deane et al. | 604/43 |
| 4,759,349 A * | 7/1988 | Betz et al. | 604/902 |
| 4,784,637 A * | 11/1988 | Ryder et al. | 604/38 |
| 4,842,581 A | 6/1989 | Davis | |
| 4,857,047 A | 8/1989 | Amoils | |
| 4,874,368 A | 10/1989 | Miller et al. | 604/191 |
| 4,891,044 A | 1/1990 | Mitchell | |
| 4,902,281 A | 2/1990 | Avoy | 604/88 |
| 4,904,238 A | 2/1990 | Williams | |
| 4,935,006 A | 6/1990 | Hasson | |
| 4,941,872 A * | 7/1990 | Felix et al. | 604/27 |
| 4,978,336 A * | 12/1990 | Capozzi et al. | 604/82 |
| 5,030,202 A | 7/1991 | Harris | 604/27 |
| 5,030,215 A | 7/1991 | Morse et al. | 604/410 |
| 5,061,180 A | 10/1991 | Wiele | |
| 5,116,315 A * | 5/1992 | Capozzi et al. | 604/82 |
| 5,120,305 A | 6/1992 | Boehringer et al. | |
| 5,145,367 A | 9/1992 | Kasten | |
| 5,290,552 A | 3/1994 | Sierra et al. | |
| 5,318,782 A | 6/1994 | Weis-Foch | |

OTHER PUBLICATIONS

Marquet, J., *J. Headand Neck Pathol.*, (1982), vol. 3, pp. 71–72.

Masri, M.A. et al., *Thromb. Hemeostas.*, (1983), vol. 49, pp. 116–119.

McCarthy, P.M., et al., *Mayo Clinic Pros.*, (1987), vol. 62, pp. 317–319.

Moesson, M.W. et al., *Biochemistry*, (1966) vol. 5, pp. 2829–2835.

O'Connor, A.F., et al., *Otolaryngol Head Neck Surg.*, (1982), vol. 90, pp. 347–348.

Panis, J. Head & Neck Pathol. 3:94–95 (1982).

Portmann, M., *J. Head and Neck Pathol.*, (1982), vol. 3, p. 96.

Redl, H. et al., "Biomaterials 1980", Winter, G.D. et al., eds. (1982), John Wiley & Sons, Ltd., pp. 669–675.

Sataloff et al., Laryngoscope (1987) 97(9):111–112.

Seelich, T., *J. Head and Neck Pathol*, (1982), vol. 3, pp. 65–69.

Siedentop, K.H. et al., *Laryngoscope*, (1985), vol. 95, pp. 1074–1076.

Silberstein, L.E. et al., *Transfusion*, (1988), vol. 28, pp. 319–321.

Staindl, O. *Ann. Otol.*, (1979), vol. 88, pp. 413–418.

Tissucol, immuno AG, specification sheet (date unknown).

Thorson, G.K. et al., *J. Surg. Oncol.*, (1983), vol. 24, pp. 221–223.

Waite et al., Biochemistry (1966) 5:2829–2835.

Weis–Fogh et al., "A device and a method for preparing autologous tissue adhesive," (date unknown).

Weisman, R.A. et al., *Laryngoscope*, (1987), vol. 97, pp. 1186–1190.

\* cited by examiner

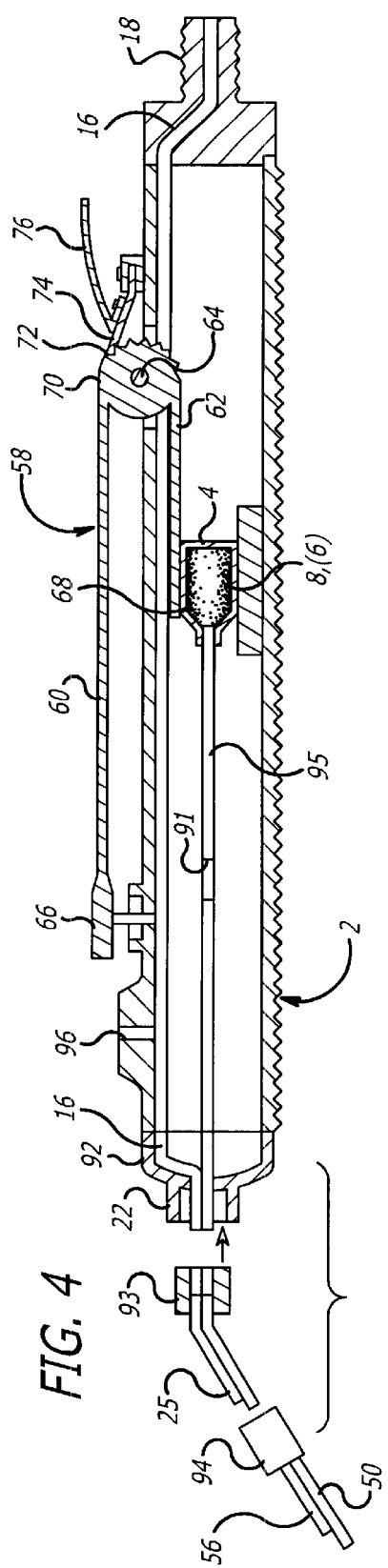
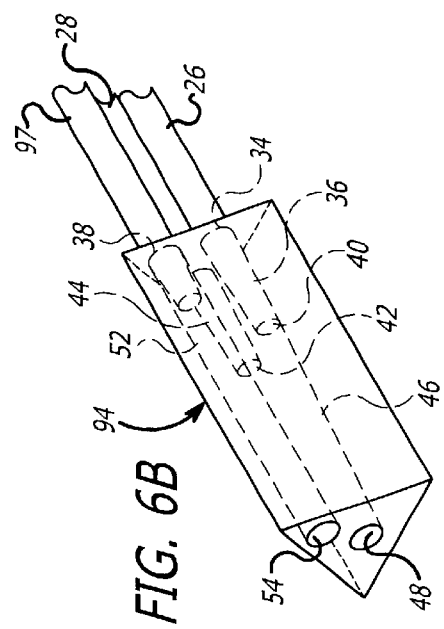
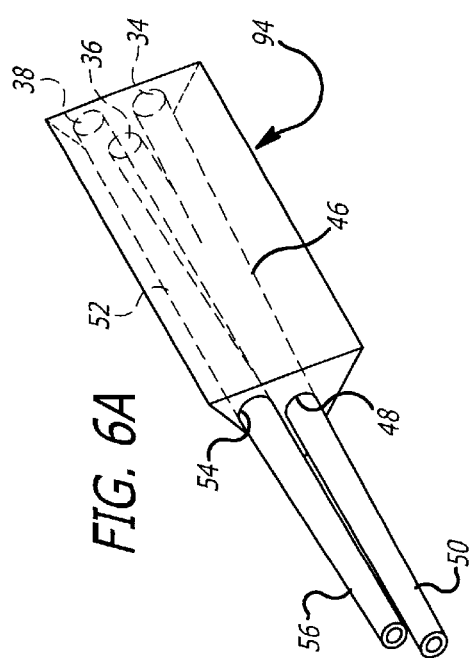

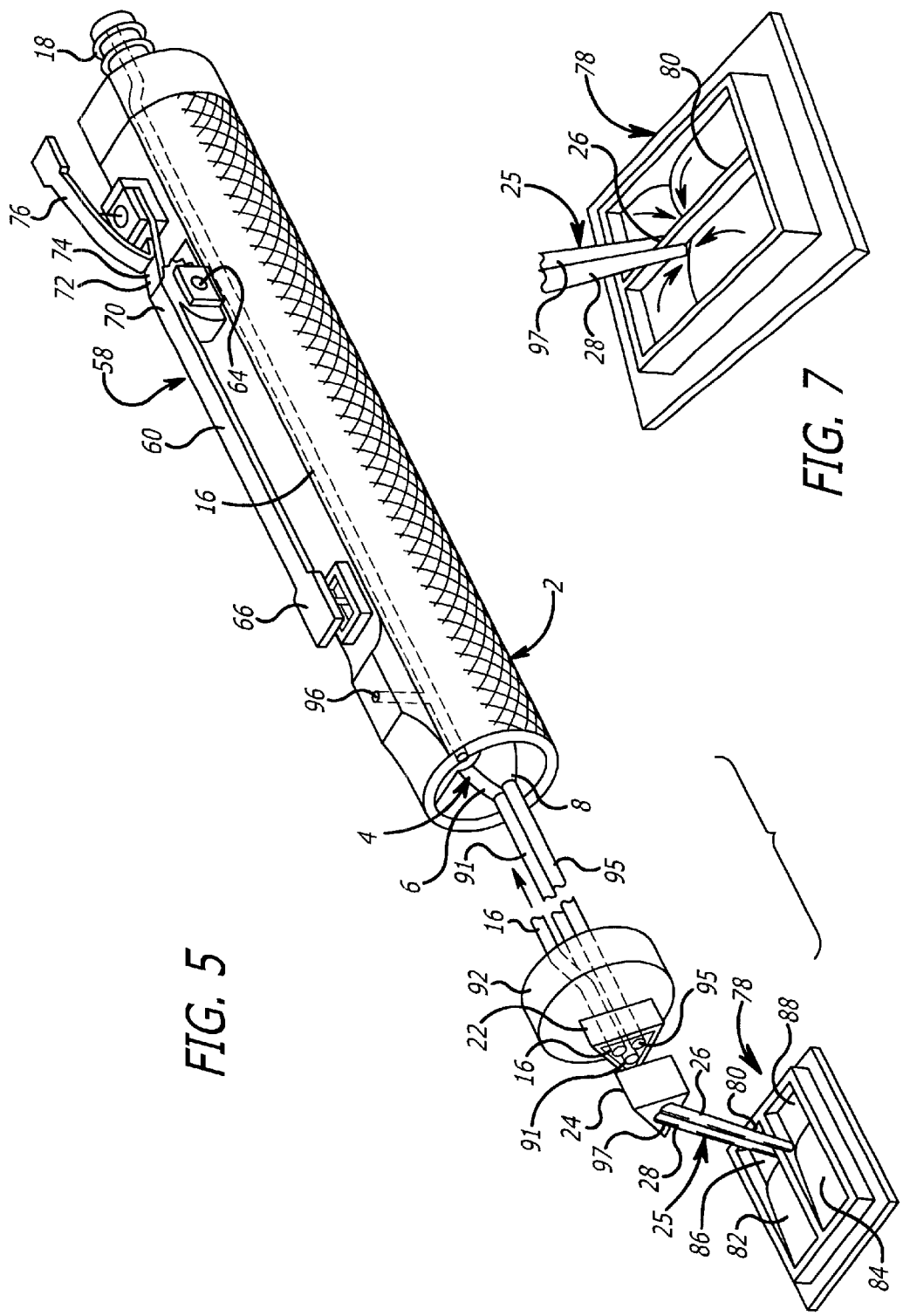

METHOD TO APPLY COMPOSITIONS TO A SURFACE

CROSS-REFERENCE TO RELATED APPLICATIONS

This application is a divisional of U.S. Ser. No. 08/703,148 filed Aug. 29, 1996, now U.S. Pat. No. 5,879,340, which is a continuation of U.S. Ser. No. 08/645,464 filed May 13, 1996, which is a continuation of U.S. Ser. No. 08/370,793 filed Jan. 10, 1995, now U.S. Pat. No. 5,648,265 which is a divisional of U.S. Ser. No. 08/090,587 filed Jul. 12, 1993, now U.S. Pat. No. 5,405,607, which is a divisional of U.S. Ser. No. 07/372,443 filed Jun. 23, 1989 and now U.S. Pat. No. 5,226,877.

TECHNICAL FIELD

The invention is related to medical and veterinary technology and procedures. More specifically, it concerns a convenient method for preparation of a fibrinogen adhesive directly from withdrawn blood.

BACKGROUND ART

The need for a suitable tissue adhesive for use in surgical procedures in human and animal medicine is well understood, and has been for nearly a century. Various substances have been tried, including completely synthetic materials such as cyanoacrylate. Because, however, the ability of the natural material fibrin to behave as an adhesive is known, fibrin powders were used for this purpose early in the development of this technology.

It has also long been recognized that the in situ formation of fibrin from fibrinogen is a preferable approach. In a relatively recent article, Staindl, O., in *Ann Otol* (1979) 88:413–418, described the use of a combination of three separately prepared substances, human fibrinogen cryoprecipitate, thrombin in the presence of calcium ion, and Factor XIII concentrate, to obtain a glue that was applied in skin graft applications, myringoplasty, repair of dural defects, hemeostatis after tonsillectomy, and tracheoplasty. Around this time, Immuno-AG, Vienna, Austria, began producing and commercializing a two-component "fibrin seal" system, wherein one component contains highly concentrated human fibrinogen, Factor XIII, and other human plasma proteins, prepared from pooled blood, and the other component supplies thrombin and calcium ion. The two components are added together in the presence of a fibrinolysis inhibitor. After application, the processes of coagulation and fibrin cross-linking occur. Eventually, the seal may lyse in the process of healing of the wound or trauma which accompanies the reconstruction of the tissue. Redl, H., et al., "Biomaterials 1980," Winter G. D., et al., eds. (1982), John Wiley & Sons, Ltd., at pages 669–675, describe the development of an applicator device for this system which mixes and applies the two components of the system simultaneously.

This two-component system has been marketed over the last ten years under the trade name Tissucol® or Tisseel®, and a number of publications have appeared describing the use of this preparation in surgical procedures. See, for example, Seelich, T., *J Head and Neck Pathol* (1982) 3:65–69; O'Connor, A. F., et al., *Otolaryngol Head Neck Surg* (1982) 90:347–348; Marquet, J., *J Head and Neck Pathol* (1982) 3:71–72; Thorson, G. K., et al., *J Surg Oncol* (1983) 24:221–223. McCarthy, P. M., et al., *Mayo Clin Pros* (1987) 62:317–319, reported the addition of barium ion to this fibrin glue system in the treatment of a bleeding duodenal sinus in order to facilitate follow-up surveillance. See also Portman, M., *J Head and Neck Pathol* (1982) 3:96; Panis, R., ibid., 94–95.

It has been recognized, of course, that the use of the commercial product, which is prepared from pooled human blood, poses at least a theoretical risk of contamination by disease-producing organisms, especially viruses. The earlier concerns were directed to transmission of hepatitis B, but more recently the focus has shifted to concern about inadvertent transfer of the AIDS virus. Therefore, attention has been given to methods to isolate an autologous counterpart of the fibrinogen-containing component in the Tissucol® system in a practical manner for use in surgery. For example, Siedentop, K. H., et al., *Laryngoscope* (1985) 95:1074–1076, describes a number of approaches to the precipitation of fibrinogen from plasma in the context of the proposed use of this material as the fibrinogen-furnishing component of a fibrin glue. Four methods were suggested: Precipitation with ethanol, use of unfractionated plasma, cryoprecipitation, and precipitation with ammonium sulfate. The first three methods were considered by the authors to be unsatisfactory; the fourth, which was the method described by Harker, L. A., et al., *New Eng J Med* (1972) 287:999–1005, was considered to have some promise.

Epstein, G. H., et al., *Anals Otol Rhinol and Laryngol* (1986) 95:40–45, suggest the use of a fibrinogen preparation from autologous plasma obtained using polyethylene glycol precipitation. These authors adapted the method of Masri, M. A., et al., *Thromb Hemeostas* (1983) 49:116–119, which involved incubation of the harvested plasma with barium sulfate and magnesium sulfate in order to remove thrombin (and thus prevent premature fibrin formation) followed by treatment of the supernatant from the resulting precipitation with a 30% solution of polyethylene glycol (PEG) of MW approximately 1000. This purified fraction was then mixed with thrombin containing calcium ion in order to form the glue. The isolation process required approximately two-three hours, but the PEG-precipitated fraction could be stored for as much as several weeks, and therefore the preparation could be made in advance of surgery. Autologous fibrinogen preparations obtained following this procedure were shown to be adhesive with implant materials by Feldman, M. C., et al., *Arch Otolaryngol—Head and Neck Surg* (1988) 114:182–185; additional applications of this approach to other surgical indications were also reported by Feldman, M. C., et al., *Arch Opthalmol* (1987) 105:963–967; Feldman, M. C., et al., *M J Otolog* (1988) 9:302–305; Silberstein et al., L. E., et al., *Transfusion* (1988) 28:319–321.

In addition, the material prepared as described by Epstein et al., by barium sulfate/magnesium sulfate precipitation followed by treatment of the supernatant with polyethylene glycol, was characterized to as to its components by Weisman, R. A., et al., *Laryngoscope* (1987) 97:1186–1190. The product was found to contain about 13–50 mg/ml of fibrinogen when the material precipitated from 50 ml blood was brought to a volume of 1 ml, wherein this concentration varies with the concentration of PEG. The percent of total protein attributable to fibrinogen ranged from 42–92 percent; the lower the PEG concentration, the higher the percentage of fibrinogen. The concentrations of kallikrein and pre-kallikrein were shown to be reduced to 1–2% of their levels in plasma in the presence of 10% PEG, and Factor XIII activity was shown to be present.

A system for preparing autologous tissue adhesive was also described by Weis-Fogh in PCT Application WO 88/02259 and WO 91/17778, which discloses a reasonably complex system based on ethanol precipitation.

General methods for preparing plasma adhesives have also been described in a series of related U.S. patents by Schwartz et al. assigned to Immuno-AG: U.S. Pat. Nos. 4,414,976; 4,298,598; 4,362,567; and 4,377,572. These methods involve cryoprecipitation of the adhesive material from plasma and various work-up procedures to obtain a mixture of defined composition. In addition, U.S. Pat. No. 4,427,650 to Stroetmann describes a preparation method involving the formation of a cryopreciptiate.

Very early studies on blood fibrinogen, unrelated to the preparation of adhesive compositions, experimented with the use of glycine as a precipitant. A 1963 paper by Kazal, L. A., et al., *Proc Sec Exp Biol Med* (1963) 10:989–994, described the use of glycine at about 2.2M at room temperature to precipitate fibrinogen after removal of the thrombin with $BaSO_4/MgSO_4$ precipitation. Moesson, M. W., et al., *Biochemistry* (1966) 5:2829–2835, recognized that fibrinogen can be directly precipitated in this manner, but did not assess the suitability of the precipitated material to behave as a controlled adhesive.

None of the foregoing methods is readily adaptable for convenient use of an autologous plasma fraction as an adhesive which can be prepared quickly in the course of the surgical procedure. All of the approaches suggested for preparation of the fibrinogen-containing fraction for this purpose are too time-consuming and complex to be finished in a short enough time period to be accomplished during the course of the surgery. Also, in some procedures, such as cryoprecipitation, special equipment, such as refrigerated centrifuges, is required. While the prior art approach is to prepare the composition in advance, this immediately imposes the necessity for additional procedures for identification and retrieval of the samples matched with the patient, and the concomitant opportunity for error, in addition to the inconvenience to the patient, who must then arrange time for an additional medical appointment. And, of course, this practice is not possible when the surgery is conducted on an emergency basis.

The present invention, by providing a surprisingly simple method and apparatus for the preparation of autologous adhesive, permits the autologous composition to be prepared in the operating room and administered at the time of preparation.

In addition to the problem of preparation, methods to administer the adhesive have not provided sufficient controls to permit clean fusions of tissue to be made. The adhesive is administered as a two-component system—the fibrinogen preparation as one component and a thrombin/$Ca^{+2}$ composition as another. The Tissucol® system uses a double-syringe arrangement wherein the two components are mixed in the injector immediately prior to dispensing. No means to remove debris or excess adhesive from the site of application is provided, and the potential for premature adhesion also exists. The present invention also provides an applicator with a premix immediately upstream of the application outlet means and a means to apply suction at the outlet to maintain the application area in condition for successful adhesion.

DISCLOSURE OF THE INVENTION

The invention provides effective means to prepared and administer autologous plasma-derived adhesive during the course of a surgical procedure. The method of the invention can also be used to prepare the adhesive under less constrained conditions, but the simplicity and ease with which the invention method results in the desired adhesive makes it adaptable to this important use.

The invention process provides the desired adhesive composition in a one-step treatment directly applicable to separated plasma using a recognized, nontoxic precipitant, such as suitable concentrations of amino acids, but preferably a nontoxic polymer such as polyvinyl alcohol (PVA) or polyethylene glycol (PEG). The fraction precipitated by these pharmaceutically acceptable reagents results in a high concentration of fibrinogen in the precipitate, along with other factors necessary for fibrin formation, as well as permitting the use of a simple, disposable apparatus to carry out the manipulations.

Thus, in one aspect, the invention is directed to a process for preparing a fibrinogen adhesive composition from whole blood, which process comprises directly contacting plasma with an amount of polyethylene glycol of molecular weight 200–8000, or other precipitant selected from the group consisting of amino acids and nontoxic hydrophilic polymers, which is effective to precipitate the fibrinogen-containing fraction. Then the precipitated fibrinogen fraction is recovered for use, either by mechanical disruption of the precipitate or pellet or by suspension in an aqueous medium.

In another aspect, the invention is directed to the fibrinogen-containing preparation obtained by the method of the invention.

In still another aspect, the invention is directed to an apparatus for preparing the fibrinogen composition consisting essentially of a device with dual separation chambers with a means for fluid communication between the chambers.

In still another aspect, the invention is directed to an applicator for injecting this or any other two-component system into a human or other animal subject which provides for simultaneous application of suction at the outlet for the components, and to a method to administer the fibrinogen composition using this apparatus.

BRIEF DESCRIPTION OF THE DRAWINGS

FIG. 4 is a longitudinal sectional view of an apparatus for administering a two-component composition to an animal subject.

FIG. 5 is a perspective view of the apparatus of FIG. 4.

FIGS. 6A and 6B are perspective views of the mixing head of the apparatus of FIGS. 4 and 5.

FIG. 7 is a perspective view of the filler tray and reservoir tip of the apparatus of FIGS. 4 and 5.

MODES OF CARRYING OUT THE INVENTION

The Adhesive Composition

Figure 1:
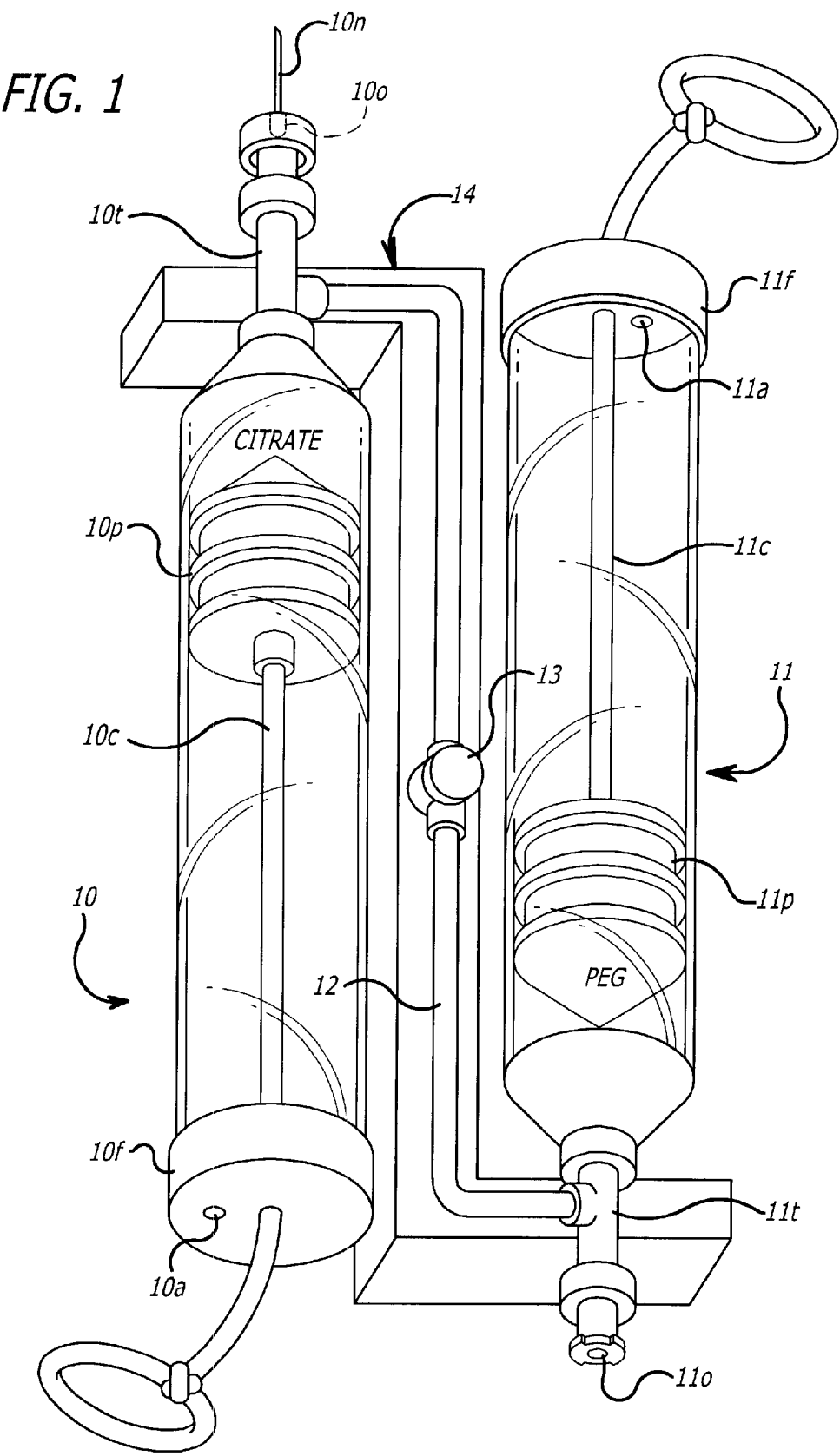
FIG. 1 is a perspective view of one embodiment of the apparatus of the invention for preparing the plasma-derived adhesive.

The adhesive composition of the invention contains substantial amounts of fibrinogen and sufficient Factor XIII to effect fibrin formation and cross-linking in the presence of added thrombin and calcium ion. Thus, as used herein, "fibrinogen adhesive composition" refers to a fraction of blood plasma which contains substantial amounts of fibrinogen and sufficient amounts of other factors required for fibrin formation that, when combined with a preparation of thrombin and calcium ion, fibrin formation and cross-linking takes place conferring on the composition the properties of a tissue adhesive.

It is believed that the formation of the adhesive occurs through the conversion of fibrinogen into fibrin monomers, which conversion is mediated by thrombin; these monomers aggregate and form a gel. Thrombin also catalyzes the transformation of Factor XIII to Factor XIII* which is activated in the presence of calcium ions to Factor XIIIa. Factor XIIIa cross-links the fibrin monomers of the gel aggregation into a polymeric state. The polymeric material adheres to tissue or bone, and continued cross-linking can occur as Factor XIIIa also cross-links fibronectin.

Therefore, the necessary components of the fibrinogen adhesive composition are fibrinogen itself and Factor XIII. Other components may also be present or may be added to modify and improve the effect of the adhesive. For example, a fibrinolysis inhibitor, such as aprotinin or aminocaproic acid can also be added. In the compositions of the invention, the levels of kallikrein and prekallikrein are greatly reduced from those present in plasma; these factors are also fibrinolytic. Other additives useful for purposes not directly related to the adhesive properties of the composition may also be included, such as various protein factors which are useful in wound healing, for example, fibroblast growth factor, platelet-derived growth factor, various angiogenic factors and the like. Other hormones, such as insulin, glucagon, steroids, and prostaglandins can also be included, resulting in a slow release system for these drugs. Also because the invention compositions may be prepared sufficiently efficiently to permit the use of an autologous fraction, other factors from plasma which aid in clotting, such as Factor VIII and immunoglobulins, are beneficial rather than detrimental when brought down with the fibrinogen precipitate. By adjusting the concentration of the precipitant and/or, in this case of a polymeric precipitant, its molecular weight, variable amounts of these factors may be included in the composition.

Preparation of the Composition

The method of the invention which provides the fibrinogen adhesive composition is straightforward and sufficiently simple that it can be used in the operating room to provide an autologous adhesive preparation. The appropriateness of the process for this application does not mean, of course, that its application is thus limited. This straightforward process can be used as well in the preparation of fibrinogen adhesive compositions in advance of surgery from autologous, designated donor, or pooled plasma sources, if desired. Furthermore, while its use is envisioned as most dramatically associated with surgery in humans, it is also suitable for veterinary uses.

The process results in a composition which has 50–80 mg/ml of fibrinogen, in general, as compared to the 2–6 mg/ml concentration in plasma or whole blood. This is a range comparable to the commercially available Tisseel® composition which contains 70–110 mg/ml. Also, like the commercial Tisseel® composition, the fibrinogen adhesives of the present invention contain sufficient Factor XIII to provide cross-linking of the fibrin obtained. There may also be present varying amounts of plasma components which are not absolutely necessary for fibrin formation but may be helpful, such as, e.g., Factor VIII, prostaglandins, and platelets.

In general, the process begins with the withdrawal of whole blood from an autologous, or other, or multiple donors in the presence of an anticoagulant, and separation of plasma from the red blood cell fraction. Typical anticoagulants include heparin and sodium citrate; others generally known in the art may also be used. If sodium citrate is used, it is generally supplied as a buffer at physiological pH with citrate ion present at 3–5%. The sodium salt is preferred. The range of means to prepare citrate and other anticoagulants suitable for primary separation of blood into red blood cells and plasma is well understood in the art. Typically, the separation can be effected by centrifugation; a suitable protocol involves spinning at about 2000–5000 g for about 5–10 minutes.

In the method of the invention, after the plasma is separated from the red blood cells, it is treated directly, at ambient temperature, without prior treatment to remove thrombin, with a physiologically acceptable nontoxic precipitant. The precipitants of the invention include the natural amino acids and nontoxic polymers, especially polyvinyl alcohol and, most preferably, polyethylene glycol. Preferred amino acids are small neutral amino acids such as glycine, serine and alanine, most preferably glycine. Most preferred among the polymer precipitants is polyethylene glycol in a molecular range of 200–8000 supplied as a concentrated solution. The precipitant is preferably supplied as a concentrated solution which, when mixed with plasma, will yield a concentration effective in precipitating the adhesive composition. Optimal concentration of the precipitant can readily be determined by routine experimentation; simple in vitro assays for fibrin formation, such as those described by Epstein, G. H., et al., *Anals Otol Rhinol and Laryngol* (1986) 287:999–1005, can be used, and fibrinogen content measured as described.

The concentrated solution or, in some instances, undiluted precipitant is added to the plasma in an amount effective to precipitate the fibrinogen adhesive composition of the invention. If PEG is used, the final concentration of PEG depends on the concentration of plasma in the precipitating solution and on the molecular weight of the PEG. A suitable and typical set of parameters utilizes an approximately 60% solution of PEG of molecular weight 1000 in saline at pH 7.4, and the plasma is added in sufficient volume (typically 10% w/v of precipitant solution/final volume) to obtain a resulting concentration of 8–15% w/v PEG in the volume of the final mixture. The plasma itself is, therefore, only slightly diluted. The precipitation takes place at room temperature and is complete essentially instantaneously, although generally it is advantageous to cure the precipitate for 5–10 min.

The precipitate containing the fibrinogen adhesive is then recovered, typically by centrifugation. The pellet may be recovered by mechanical disruption or resuspended in normal saline for use at a concentration of about 50 mg/ml–80 mg/ml of fibrinogen. Typically from about 60 cc of whole blood a fibrinogen adhesive composition which would contain 30–50 mg fibrinogen when resuspended to 1.5 ml is obtained.

The use of the amino acids and biocompatible polymers as precipitant has considerable advantage over the prior art use of ethanol and cryoprecipitation. The resulting concentration of fibrinogen is markedly higher, and the precipitants are recognized material safe for internal use. For example, PEG has been used as a lubricant or conditioner in ointments and in pharmaceutical and cosmetic preparations, including injectables. It is a water-soluble, nonvolatile material of no known clinical toxicity. The amino acids are, of course, nontoxic metabolites and are common components of pharmaceutical compositions.

Because of the benign nature of the precipitant, the remaining supernatant plasma fraction, which contains platelets and white blood cells, can be reused for other purposes; similarly, the red blood cells removed could, if desired, be returned to the patient.

Isolation apparatus

The process of the invention can be conducted using standard laboratory and medical equipment. For example, the blood may simply be withdrawn into a syringe containing anticoagulant and emptied into a centrifuge tube for separation. The supernatant plasma can then be removed by a syringe containing the precipitant or can be pipetted into a separate vessel and the precipitant added. The suspension can then be centrifuged using standard equipment and the precipitated material disrupted or resuspended by addition of saline after removal of the supernatant.

It is evident, however, that the use of standard equipment adds complexity to the process and imposes requirements for sterilization of the various pieces of apparatus and maintenance of integrity of the sample. The invention apparatus provides a simple design which eliminates these complexities and streamlines the process.

The invention apparatus contains two chambers, both of which can be used directly in a laboratory or medical centrifuge. The first chamber is designed to effect the separation of plasma and red blood cells; the second chamber provides a method to separate the fibrinogen adhesive composition from the supernatant plasma fraction. Because a means of fluid communication is provided between the first and second chamber, the plasma obtained in the first chamber can be made the subject of fibrinogen adhesive separation in the second, and the supernatant from the precipitate can be returned to the first chamber. The first chamber generally contains an effective amount of anticoagulant; the second chamber contains an effective amount of precipitant such as polyethylene glycol solution to effect precipitation of the fibrinogen adhesive. The apparatus, then, comprises a first and second chamber, a means of fluid communication between the first and second chambers and a means to interrupt this communication, wherein the first chamber contains anticoagulant and the second chamber contains the precipitant and permits the removal of the precipitate.

One convenient embodiment of the apparatus of the invention is shown in FIG. 1. In this embodiment, the apparatus consists of two especially adapted syringe bodies 10 and 11 interconnected by a supported tube 12. The tube is provided with a valve 13 which is capable of turning on and off the flow of fluid between chambers 10 and 11. Both of the chambers are fitted onto the frame and locked onto a tube having a T-joint at 10t and 11t. Both syringe cylinders are provided with a modified plunger 10p and 11p which may be withdrawn by a pulling means such as a plastic cord 10c and 11c causing the withdrawal of the plunger to a position flush with the ends of the cylinders where the top of the plunger is sealed by a flange (10f and 11f) when withdrawn to a fully extended position. This permits the syringe bodies to be used as centrifuge tubes when the plunger is fully withdrawn to the end of the syringe and sealed at the flange. While the plunger could be returned to the position toward the tip of the syringe by use of a rod inserted at the apertures 10a and 11a, this is generally not necessary as the material in the chamber can be removed by suction, provided either by the adjacent chamber or by the application of a vacuum at the chamber outlet. Thus, withdrawal of the plunger in the chamber 11 with valve 13 open and the outlets 10o and 11o sealed results in transfer of the liquid from chamber 10 to chamber 11. Both syringes can be detached from the supporting frame 14 by release of the locks to the T-tube, and can be sealed if appropriate.

In use, the plasma separation chamber 10 is fitted with a needle 10n which is inserted into the subject for withdrawal of blood. The valve 13 is closed during this step, thus preventing the formation of a vacuum in the connecting tube 12 and confining the flow of blood to the chamber 10 when the plunger 10p is withdrawn by pulling the cord 10c. The size of the plunger is adjusted to permit withdrawal of a predetermined amount of blood, typically 60 cc. The chamber 10 is previously supplied with sufficient citrate buffer to obtain a concentration of about 4% citrate ion when the predetermined amount of blood is withdrawn.

When the blood is withdrawn into chamber 10, the needle is detached, the outlet 10o sealed with a sealing cap, and the device removed to a centrifuge with a head designed to accommodate this device, or, if desired, chamber 10 is detached for centrifugation independently. The application of 4500 g for 5–10 minutes results in a separation of the red blood cells from the plasma. If the device is placed intact into the centrifuge, the plunger of chamber 11 is unaffected as the outlet of chamber 11, shown as 11o, is sealed and the PEG contained in this chamber is not compressible.

After centrifugation, the valve 13 is opened and the plunger 11p is withdrawn and sealed at flange 11f, thus transferring the plasma into chamber 11. Chamber 11 is presupplied with an approximately 60% PEG solution of molecular weight 1000, or a comparable concentration of an alternate molecular weight sufficient to effect precipitation of the fibrinogen adhesive. The motion of the plungers is stopped when the red blood cells reach the upper portion of the chamber 10. The valve 13 is then closed.

If desired, the red blood cells remaining in chamber 10 can be withdrawn or expelled and returned to the patient.

The apparatus is then agitated, if necessary, to intermix the PEG with the plasma. Outlet 11o remains sealed. The chamber 11 is then centrifuged either within the device or after removal therefrom to separate the precipitate from the supernatant plasma. The apparatus is, of course, inverted from the position shown in FIG. 1. After about 15–20 minutes at 6000–10,000 g sufficient separation of precipitate has occurred. The chamber 11 is replaced in the apparatus if it has been removed, and the valve 13 again opened while the outlet 11o remains sealed. The supernatant is then withdrawn into chamber 10 by withdrawal of plunger 10p (outlet 10o remains closed) until the fibrinogen precipitate begins to enter the connecting tube 12; valve 13 is then closed.

The fibrinogen adhesive is removed for use from chamber 11 by further reinsertion of the plunger 11p, or preferably by withdrawal into the syringe attached at the outlet 11o. If desired, the fibrinogen adhesive can be diluted in saline and the composition quantitatively removed from chamber 11 by washing.

It should be noted that chamber 10 now contains all blood components except the fibrinogen adhesive composition and contains as added components only anticoagulant and the clearly nontoxic PEG. Therefore, the modified blood in chamber 10 could, if necessary, be used for other purposes or returned to the patient.

Figure 2:
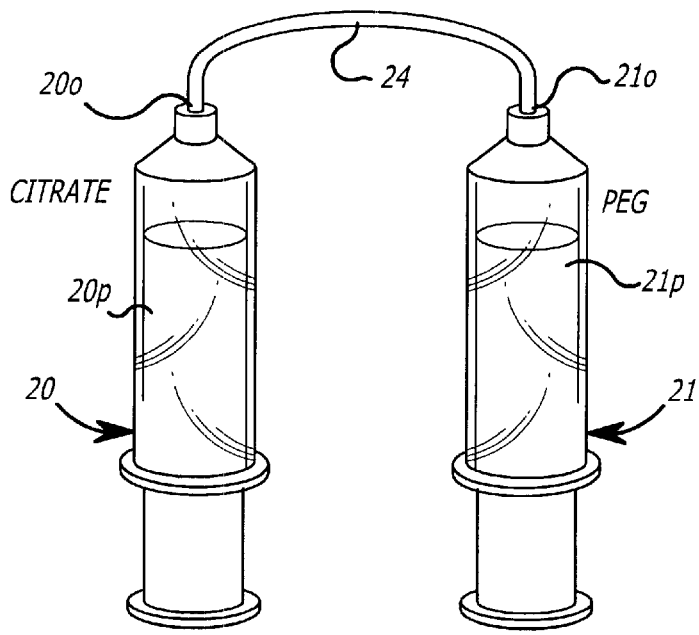
FIG. 2 is an alternative embodiment of the isolation apparatus of the invention.

FIG. 2 shows an alternative embodiment of the apparatus of the invention which dispenses with the need for the frame 14. This apparatus consists essentially of two syringes with detachable plungers and a Luer-locked connector. This embodiment has the advantage of utilizing standard medical equipment but the disadvantage of utilization of several separate parts.

In the apparatus of FIG. 2, the blood separation syringe 20, is fitted with a needle for the withdrawal of blood. Again, chamber 20 is supplied with a premeasured quantity of citrate which, when mixed with the withdrawn blood will result in a citrate buffer of about 4% citrate ion. When the plunger is retracted and chamber 20 contains whole blood, the needle and the extended portion of the plunger are detached to permit the syringe body and sealed end to be placed in a centrifuge, with the Luer lock outlet 20o sealed. Suitable syringes with plungers which can be detached and the body sealed for centrifugation of the syringe body are available commercially. The syringe barrel 20 is then centrifuged as described above, the Luer lock at outlet 20o is engaged by the interconnecting tube 24, and the plunger is replaced. With the syringe in the inverted position, the interconnector 24 is attached to a second similarly constructed syringe 21 at Leur lock 21o. Syringe 21 contains a premeasured quantity of PEG. Plasma is transferred from chamber 20 to chamber 21 through retraction of the plunger 21p which causes effective reinsertion of plunger 20p. When red blood cells begin to enter the interconnector, an event which is readily observable, the interconnector 24 is detached from chamber 21 and the mixture of plasma and PEG in chamber 21 agitated if necessary. Syringe 21 is then prepared for centrifugation by removal of the extended portion of the plunger and sealing of the body of the syringe, and closure at lock 21o, and the fibrinogen adhesive and plasma are separated under the centrifugation conditions described above. The interconnector 24 and plunger 21p are then put back in place and the plasma supernatant withdrawn into chamber 20 by retraction of plunger 20p. When fibrinogen adhesive precipitate begins to enter the interconnector, the interconnector is detached and the fibrinogen adhesive expelled into diluent, or diluent is withdrawn into chamber 21 through lock 21o.

In either case, the resuspended fibrinogen adhesive is placed in a suitable applicator for use.

Figure 3:
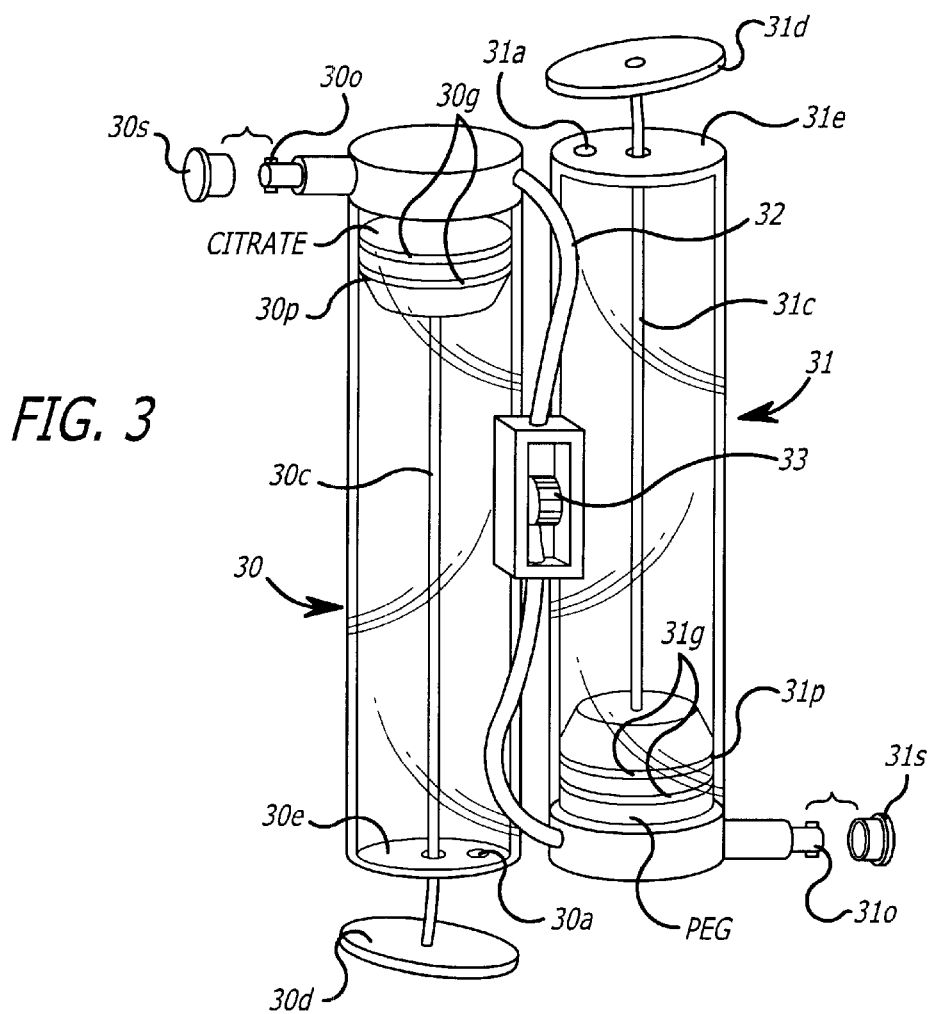
FIG. 3 is an additional alternative embodiment of the isolation apparatus of the invention.

FIG. 3 shows a third embodiment of the apparatus for isolation of the fibrinogen adhesive. Chambers 30 and 31 are connected through the tubing 32, which is regulated by a valve 33. Any suitable type of valve can be used; as shown in FIG. 3, valve 33 operates by sliding the roller so as to pinch off the tubing 32.

Chambers 30 and 31 are attached to each other by sealing or by forming the chambers using the same mold; the chambers are, as before, preloaded with suitable amounts of anticoagulant (chamber 30) and precipitant (chamber 31). Chambers 30 and 31 are provided with outlets 30o and 31o at the sides of the chambers, as shown. Outlet 30o is a Leur lock designed to accommodate a needle as ordinarily attached to a syringe. Outlet 31o is a Leur lock designed to accommodate an externally attached syringe body. Both outlets 30o and 31o have detachable sealing caps 30s and 31s.

The chambers 30 and 31 have plungers 30p and 31p which are sealed with gaskets 30g and 31g to the sides of the chambers. When fully withdrawn, the plungers are snug against the end plates 30e and 31e at the bases of the chambers. The plungers are withdrawn by a flexible plastic cord 30c and 31c, which are provided with disks 30d and 31d to aid in the withdrawal. Additional apertures 30a and 31a permit insertion of rigid rods to push the plungers forward, if required; however, the movement of the plungers is generally effected by application of a vacuum either by withdrawal of the plunger in the adjacent chamber or by an externally attached syringe.

The operation of the apparatus as shown in FIG. 3 is substantially analogous to that shown in FIG. 1. In a typical procedure, the patient's blood, about 60 cc, is withdrawn into chamber 30 with valve 33 and outlet 31o both closed. Outlet 30o is then sealed, the apparatus is placed in a centrifuge, and the plasma and red blood cells in chamber 30 are separated. Valve 33 is then opened and plunger 31p is withdrawn until the red blood cells are seen entering the tubing 32. Valve 33 is closed, and the apparatus is agitated, if necessary, and inverted and centrifuged to separate the fibrinogen adhesives from the supernatant plasma. The red blood cells in chamber 30 may be returned to the patient by an attached needle and pushing the plunger 30p prior to centrifugation, if desired.

After centrifugation, the valve 33 is again opened and plunger 30p withdrawn to draw the supernatant into chamber 30. Withdrawal of the plunger is stopped as soon as the supernatant has left chamber 31.

Outlet 31o is opened and a syringe body attached. The fibrinogen adhesive pellet is disrupted, for example, by repeated motion of the syringe plunger, and, if desired, saline may be included in the attached syringe to achieve quantitative transfer of the fibrinogen adhesive. The adhesive composition is then placed in a suitable applicator for administration to the subject.

Administration and use

The fibrinogen adhesive composition of the invention is useful in medical and veterinary applications generally comparable to those known in the art for the commercially available product Tissucol®. Commercial preparations of thrombin and calcium ion for admixture with the fibrinogen adhesive of the invention are commercially available and are used as is generally known in the art.

In a particularly advantageous way to apply the two components of the sealant to the tissue to be cemented, a dual-barreled applicator with one barrel for supply of the fibrinogen adhesive and the other for the thrombin/calcium ion mixture is employed wherein the outlet of each barrel is proximal to a suction device so that the surface prior to application can be instantly cleaned and excess components immediately removed.

Although the premixing of the components for this purpose is known in the art, as described in U.S. Pat. No. 4,359,049, incorporated herein by reference, the advantages of simultaneous application of suction for controlling the environment of the application have not been recognized. To applicants' knowledge, the only medical devices which simultaneously permit application of a material and suction are devices designed for irrigation, such as that described in U.S. Pat. No. 4,229,221, where a fluid is applied and then removed from a target tissue, especially in dental applications, for cleansing purposes.

In the present application, the provision of suction at the site of sealant application permits the withdrawal of interfering substances as well as control of the quantity of sealant applied. Thus, although the commercially available Duploject device can be used for application, the modified adhesive applicator described hereinbelow is highly advantageous. This device is designed to permit controlled application of both fibrinogen adhesive and thrombin/calcium mixture with premixing of these components immediately prior to injection along with a means to produce suction for surface cleaning and excess sealant removal.

A particularly advantageous design of such an applicator is shown in FIGS. 4–7 herein, and was described in U.S. Ser. No. 06/683,621 filed Dec. 19, 1984 by the Applicant, and now abandoned.

In more detail, FIGS. 4 and 5 show a housing 2 which resembles a pen in both size and shape, and which is held in a similar fashion. The interior of the housing 2 includes a chamber 4 having walls that are sufficiently flexible so that the chamber 4 may be compressed by a relatively slight amount of external pressure. At the same time, the walls of the chamber 4 are sufficiently resilient so that, in the absence of external pressure, the chamber 4 will return to its original volume and configuration. The chamber 4 is divided into a first compartment 6 and a separate but identical second compartment 8. In application of the composition of the invention to a subject, one chamber (6) contains the fibrinogen adhesive composition and the other (8) contains the thrombin/$Ca^{+2}$ preparation. In the preferred embodiment of the present invention, the chamber 4 consists of a rubber bulb, although it is recognized that any chamber whose volume may be easily reduced and expanded may serve as the chamber 4.

The first compartment 6 of the chamber 4 is connected to a first liquid channel 91 which runs lengthwise through the interior of the housing 2 and which terminates at the housing end piece 92. The second compartment 8 of the chamber 4 is likewise connected to a second liquid channel 95 which runs parallel to the first liquid channel 91 and which similarly terminates at the housing end piece 92.

The housing end piece 92 is fitted with an adaptor 22 which is configured to receive a connector 24 or 93 of a detachable channel extension 25. The channel extension 25 includes two liquid channels 26 and 28 (and a suction channel 97 to be described below). When the channel extension 25 is attached to the housing end piece 92 by means of the adapter 22 and the connector 24 or 93, the liquid channels 28 and 26 serve as extensions, respectively, of the fluid channels 91 and 95 and as reservoirs for the fibrinogen adhesive and the $Ca^{+2}$/thrombin preparation.

The channel extension 25 may be configured in a variety of lengths and shapes, depending upon the particular requirements of the applicator. The use of a detachable channel extension 25 allows a single applicator housing 2 to be used in conjunction with a variety of differently configured channel extensions 25.

The present invention also includes a mixing head 94 (see FIGS. 6A and 6B). The mixing head 94 includes three entry ports of which two, 34 and 36, are configured to be attached respectively to the distal ends 40 and 42 of the liquid channels 26 and 28.

The interior of the mixing head 94 includes a Y-shaped channel 46 which connects the entry ports 34 and 36 with the exit port 48. The liquid adhesive components dispensed through the entry ports 34 and 36 are thereby combined in the channel 46 before being ejected through the single exit port 48. A single adhesive channel tube 50 is connected to the exit port 48, thus permitting the premixed adhesive to be applied.

The apparatus as shown in FIGS. 4 and 5 includes a suction channel 16 which is incorporated into the wall of the housing 2 and which runs parallel to the first and second liquid channels 91 and 95. Suction channel 16 also terminates at the housing end piece 92. The proximal end of the suction channel 16 is surrounded by an adaptor 18 which is configured to connect the suction channel 16 to a remote vacuum source (not shown).

Operation of the suction channel 16 is controlled by means of a venturi opening 96 which is located on the exterior of the housing 2. Obstruction is the venturi opening 96 permits the suction force which originates at the remote vacuum source to be conducted through the length of the section channel 16.

The interior of the mixing head 94, shown in FIGS. 6A and 6B, also includes a channel 52 which connects the entry port 38 with an exit port 54. The channel 52 serves to conduct the suction force from the distal end 44 of the suction channel 97 to the exit port 54. A single suction channel tube 56 is connected to the exit port 54.

The suction channel tube 56 is shorter than the adhesive channel tube 50 so that the suction channel tube 56 does not interfere visually or functionally with the application of the adhesive. Materials from the site of application, when suctioned, are drawn along the exterior surface of the adhesive channel tube 50 to the orifice of the suction channel tube 58. This provides gentle, atraumatic suction required in microsurgery.

In the apparatus of FIGS. 4 and 5, compression and expansion of the bulb 4 is controlled by means of a leverage mechanism 58. The leverage mechanisms 58 includes an outer lever arm 60 and an inner lever arm 62. Both lever arm 60 and lever arm 62 turn about a fulcrum 64.

The free end 66 of the outer lever arm 60 is positioned adjacent the venturi opening 96 of the suction channel 16. This placement allows the operator to switch rapidly and with a minimum amount of movement from the control of the venturi opening 96 to the control of the lever arm 60.

The free end 68 of the inner lever arm 62 rests against the exterior of the flexible tube 4. Movement of the free end 68 of the inner lever arm 62 toward the bulb 4 will cause both compartments 6 and 8 of the bulb 4 to be compressed in equal amounts, thereby causing a small quantity of air to be displace from each of the compartments 6 and 8 through the liquid channels 91 and 95, respectively. Movement of the free end 68 of the inner lever arm 62 away from the bulb 4 will allow the resilient bulb material to return to its original dimensions.

The lateral motion of the free end 66 of the outer lever arm 60 that is transferred to the free end 68 of the inner lever arm 62 is proportional to the relative lengths of the outer lever arm 60 and inner lever arm 62. If the inner lever arm 62 is shorter than the outer lever arm 60, as shown in FIGS. 4 and 5, then a relatively large lateral motion of the free end 66 will be translated into a relatively short lateral motion of the free end 68. In this manner, a relatively broad finger-controlled lateral movement of the lever arm 60 may be used to control a relatively small displacement of air through each of the liquid channels 91 and 95.

The pivot ends of both the outer lever arm 60 and the inner lever arm 62 are fixed to a ratchet wheel 70. The rotational axis of the ratchet wheel 70 is concentric with the fulcrum 64. Disposed about a portion of the circumference of the ratchet wheel 70 is a set of spaced ratchet teeth 72.

A pawl 74 is positioned to engage the ratchet teeth 72, and to thereby prevent movement of the ratchet wheel 70 in a clockwise direction as shown in FIG. 4. A finger-operable pawl release 76 is attached to the pawl 74. The pawl release 76 provides a mechanism for disengaging the pawl 74 from the ratchet teeth 72, thereby allowing unrestricted movement of the ratchet wheel 70.

The combination of the ratchet wheel 70 and pawl 74 thereby provides a mechanism for stopping movement of the lever arms 60 and 62 (as well as compression or expansion of the bulb 4) at a plurality of fixed intervals. The size of these intervals is dependent on the spacing between the teeth 72 and the circumference of the ratchet wheel 70.

In the apparatus shown, the two components of the dual-component adhesive are drawn into the channels 26 and 28 from a filler tray 78 shown in FIG. 7. The filler tray 78 is designed to orient the operator so that the possibility of drawing a liquid component into the incorrect channel is minimized.

The filler tray 78 is generally of rectangular configuration and divided by a septum 80 along the center of its longer axis into a first container 82 and second container 84. The floor of the first container 82 has a trough 86 which is perpendicular to the septum 80. The floor of the second container 84 has a similar trough 88 which is also perpendicular to the septum 80. Both troughs 86 and 88 are located closer to one end of the filler tray 78 than the other. The resulting asymmetry of the filler tray 78 provides a useful visual orientation for the operator. Both troughs 86 and 88 slant downward toward the septum 80, so that even a small amount of liquid placed in either container 82 or 84 will pool towards the septum 80.

The height and width of the septum 80 are selected so that the distal end 40 of the channel 26 will rest in the lowest part of the trough 88 at the same time that the distal end 42 of the channel 28 will rest in the lowest end of the trough 86. In this way, even small amounts of liquid in the containers 82 and 84 will be directed to the distal ends 40 and 42 of the channels 26 and 28. The height of the septum 80 is selected so that the distal end 44 of the suction channel 97 rests above the septum 80 when fluid is drawn from the filler tray 78, the points at which the distal ends 40 and 42 of the channels 26 and 28 rest adjacent to the septum 80 are the lowest of all points in the filler tray 78. In this way any fluid placed in either container 82 or 84 of the tray 78 will pool towards the distal ends 40 and 42 during the filling of channels 26 and 28.

The filler tray 78 is anchored to a heavyweight base 90 to help prevent the liquid contents of the filler tray from being spilled.

To operate the device, the outer lever arm 60 is first pressed toward the housing 2 so that the fulcrum 64 rotates in a counterclockwise direction as shown in FIG. 4. The free end 68 of the inner lever arm 62 is thereby forced against the exterior of the bulb 4, compressing the bulb. The free end 68 of the lever arm 62 will be held in place against the bulb 4 by means of the pawl 74 engaging the ratchet teeth 72 of the ratchet wheel 70.

The distal ends 40 and 42 of the fluid channels 26 and 28 are then placed into the corresponding containers 82 and 84 of the filler tray 78. The pawl release 76 is operated to disengage the pawl 74 from the ratchet teeth 72. The ratchet wheel 70 is thereby allowed to rotate freely about the fulcrum 64.

In the absence of pressure exerted by the free end 68 of the inner lever arm 62, the resilient flexible material of the bulb 4 will return to its initial configuration, creating a pressure differential between the interior of the bulb 4 and the ambient atmosphere. Atmospheric pressure will force the liquid contents of the filler tray containers 82 and 84 into the corresponding fluid channels 40 and 42 in a volume approximately equal to that of the air originally displaced from the bulb 4.

The distal ends 40 and 42 of the fluid channels 26 and 28 are then removed from the containers 82 and 84 of the filler tray 78. The mixing tip 94 is then attached to the fluid channels 26 and 28 and the suction channel 97. The mixing tip 94 is brought to the work surface. If cleaning of the surface is desired immediately before application of the adhesive, then the venturi opening 96 of the suction channel 16 is closed off by the operator's finger. The suction force created by a remote vacuum attached to the proximal end of the suction channel is transmitted via suction channel 16 to the work surface. Fluid and debris on the work surface is thereby removed through the suction channel 16.

The precise amount of adhesive deposited on the work surface is accurately controlled via the leverage mechanism 58. As the outer lever arm 60 is pressed, the ratchet teeth 72 will rotate past the pawl 74. As each ratchet tooth passes the pawl 74, an audible "click" will be heard.

The ratchet teeth 72 may be positioned so that each "click" represents the deposit of a predefined amount of adhesive. For example, if the ratchet teeth 72 are positioned so that each "click" corresponds to the deposit of one microliter of adhesive, then an operator wishing to apply precisely three microliters of adhesive will press the outer lever arm 60 until three "clicks" are heard. The operator's visual attention to the work area thereby remains uninterrupted.

At any point during the procedure, application of the adhesive may be halted by merely removing finger pressure from the outer lever arm 60. The lever arm 60 will be maintained in position by the pawl 74 engaging the ratchet teeth 72.

In any event, the fibrinogen adhesive of the invention is applied along with a calcium/thrombin composition as understood by the art by any suitable application means.

What is claimed is:

1. A method of applying an adhesive to a work surface on a subject, the method comprising applying to said work surface a suction force from a remote vacuum source connected with a suction channel, to prepare the work surface for the application of adhesive, the suction channel being a component of an applicator device, followed by depositing said adhesive from said applicator device via a dispensing channel, the dispensing channel also being a component of said applicator device, onto said work surface, wherein the suction channel is disposed adjacent the dispensing channel and interferes neither visually nor functionally with the dispensing of adhesive from the dispensing channel, and wherein the amount of adhesive dispensed is measured audibly.

2. The method of claim 1 wherein the applicator comprises a manually operable dispensing actuator capable of emitting an audible tone at intervals to indicate the amount of adhesive dispensed, the method comprising dispensing a measured quantity of adhesive by operating the dispensing actuator until the number of tones indicative of the measured quantity is heard.

3. A method of applying an adhesive to a work surface wherein an applicator comprises a finger-operable suction control valve and a finger-operable dispensing actuator, said finger-operable suction control valve positioned adjacent to the suction control valve, and wherein the method comprises:

a) operating the finger-operable suction control valve with one finger to apply to said work surface a suction force through said suction channel, said suction channel in communication with a remote vacuum source, the suction channel being a component of an applicator device;

b) moving the one finger from the finger-operable suction control valve to the finger-operable dispensing actuator; and c) operating the finger-operable dispensing actuator with the one finger to dispense adhesive to the prepared work surface via a dispensing channel, the dispensing channel also being a component of said applicator device, wherein the suction channel is disposed adjacent the dispensing channel and interferes neither visually nor functionally with the dispensing of adhesive from the dispensing channel.

4. The method of claim 3 wherein the method comprises rapidly switching from control of the suction valve to control of the dispensing actuator.

5. The method of claim 3 wherein the suction control valve comprises a venturi opening communicating the suction supply with atmosphere, and the method comprises closing the venturi opening with the operator's finger to apply suction.

6. The method of claim 3 wherein the method further comprises:
   d) moving the one finger back to the suction control valve; and
   e) applying suction to the sealant dispensed on the work surface.

7. A method of applying a two-component adhesive system to a work surface, the method comprising:
   providing an applicator device having a suction channel and a dispensing channel, said suction channel disposed adjacent to said dispensing channel, and wherein said suction channel interferes neither visually not functionally with a dispensing of adhesive from said dispensing channel;
   applying to said surface a suction force from a remote vacuum source attached to said suction channel; and
   depositing an adhesive formed from said two components from said applicator device via said dispensing channel onto said work surface, wherein the amount of adhesive dispensed is measured audibly.

8. The method of claim 7 wherein the applicator comprises a manually operable dispensing actuator capable of emitting an audible tone at intervals to indicate the amount of adhesive dispensed, the method comprising dispensing a measured quantity of adhesive by operating the dispensing actuator until the number of tones indicative of the measured quantity is heard.

9. A method of applying an adhesive to a work surface wherein an applicator comprises a finger-operable suction control valve and a finger-operable dispensing actuator, said finger-operable suction control valve positioned adjacent to the suction control valve, and wherein the method comprises:
   a) operating the finger-operable suction control valve with one finger to apply to said work surface a suction force through said suction channel, said suction channel in communication with a remote vacuum source, the suction channel being a component of an applicator device;
   b) moving the one finger from the finger-operable suction control valve to the finger-operable dispensing actuator; and
   c) operating the finger-operable dispensing actuator with the one finger to dispense adhesive to the prepared work surface via a dispensing channel, the dispensing channel also being a component of said applicator device, wherein the suction channel is disposed adjacent the dispensing channel and interferes neither visually nor functionally with the dispensing of adhesive from the dispensing channel.

10. The method of claim 9 wherein the method comprises rapidly switching from control of the suction valve to control of the dispensing actuator.

11. The method of claim 9 wherein the suction control valve comprises a venturi opening communicating the suction supply with atmosphere, and the method comprises closing the venturi opening with the operator's finger to apply suction.

12. The method of claim 9 wherein the method further comprises:
   d) moving the one finger back to the suction control valve; and
   e) applying suction to the sealant dispensed on the work surface.

13. A method of applying a two-component fibrin sealant to a work surface, the method comprising:
   providing a handheld sealant applicator having two sealant chambers containing two sealant components, and having at least one dispensing tube for dispensing the sealant components and a suction tube connectable with a suction source for applying suction to the work surface; and
   actuating said handheld applicator to dispense said sealant; and
   audibly measuring the amount of sealant dispensed.

14. The method of claim 13 wherein the applicator comprises a manually operable dispensing actuator capable of emitting an audible tone at intervals to indicate the amount of adhesive dispensed, the method comprising dispensing a measured quantity of adhesive by operating the dispensing actuator until the number of tones indicative of the measured quantity is heard.

15. A method of applying a two-component fibrin sealant to a work surface wherein an applicator comprises a finger-operable suction control valve and a finger-operable dispensing actuator, said finger-operable suction control valve positioned adjacent to the suction control valve, and wherein the method comprises:
   a) operating the finger-operable suction control valve with one finger to apply to said work surface a suction force through said suction channel, said suction channel in communication with a remote vacuum source, the suction channel being a component of an applicator device;
   b) moving the one finger from the finger-operable suction control valve to the finger-operable dispensing actuator; and
   c) operating the finger-operable dispensing actuator with the one finger to dispense adhesive to the prepared work surface via a dispensing channel, the dispensing channel also being a component of said applicator device, wherein the suction channel is disposed adjacent the dispensing channel and interferes neither visually nor functionally with the dispensing of adhesive from the dispensing channel.

16. The method of claim 15 wherein the method comprises rapidly switching from control of the suction valve to control of the dispensing actuator.

17. The method of claim 15 wherein the suction control valve comprises a venturi opening communicating the suction supply with atmosphere, and the method comprises closing the venturi opening with the operator's finger to apply suction.

18. The method of claim 15 wherein the method further comprises:
   d) moving the one finger back to the suction control valve; and
   e) applying suction to the sealant dispensed on the work surface.

19. A method of applying a two-component fibrin sealant to a work surface wherein an applicator comprises a finger-operable suction control valve and a finger-operable dispensing actuator, said finger-operable suction control valve positioned adjacent to the suction control valve, and wherein the method comprises:
   a) providing an applicator having a pivotally mounted manually operable dispensing lever coupled to sealant component chambers for dispensing the sealant components with a reduced mechanical displacement;

b) manually moving the dispensing lever to dispense a desired quantity of the sealant component; and c) releasing the dispensing lever to terminate dispensing of the sealant components.

20. A method of applying a two-component fibrin sealant to a work surface of an animal subject, the method employing a handheld sealant applicator having two chambers to contain the two sealant components, at least one dispensing tube for dispensing the sealant components to the subject, and a pivotally mounted manually operable dispensing lever coupled with the sealant component chambers for dispensing the sealant components with a reduced mechanical displacement, the method comprising:

a) manually moving the dispensing lever to dispense a desired quantity of the sealant components; and b) releasing the dispensing lever to terminate dispensing of the sealant components.

21. The method of claim 20 wherein the applicator comprises a suction tube connectable with a suction source for applying suction to the work surface and the method further comprises preparing the work surface for application of adhesive by applying suction to the work surface through the suction tube.

* * * * *